(12) United States Patent
Parisien et al.

(10) Patent No.: US 11,577,044 B2
(45) Date of Patent: Feb. 14, 2023

(54) HYPNOTHERAPY SYSTEM UTILIZING AN INTERACTIVE DOLL AND METHOD OF HYPNOTHERAPY FOR CHILDREN

(71) Applicants: Lisa L. Parisien, Papillion, NE (US); Amanda J. Olmscheid, Omaha, NE (US)

(72) Inventors: Lisa L. Parisien, Papillion, NE (US); Amanda J. Olmscheid, Omaha, NE (US)

(73) Assignee: Lisa Parisien, Papillion, NE (US)

( * ) Notice: Subject to any disclaimer, the term of this patent is extended or adjusted under 35 U.S.C. 154(b) by 788 days.

(21) Appl. No.: 16/575,088

(22) Filed: Sep. 18, 2019

(65) Prior Publication Data

US 2021/0077770 A1 Mar. 18, 2021

(51) Int. Cl.
*A61M 21/00* (2006.01)
*A63H 3/00* (2006.01)
(Continued)

(52) U.S. Cl.
CPC ............ *A61M 21/00* (2013.01); *A63H 3/003* (2013.01); *A63H 3/28* (2013.01); *G06F 3/162* (2013.01);
(Continued)

(58) Field of Classification Search
CPC ......... A61M 21/00–02; A63H 2200/00; A63H 3/00–52
See application file for complete search history.

(56) References Cited

U.S. PATENT DOCUMENTS

| 3,370,855 A | 2/1968 | Lindsay |
| 4,846,693 A | 7/1989 | Baer |

(Continued)

OTHER PUBLICATIONS

Magical Child Hypnosis, https://magical-child-hypnosis.com (Year: 2018).*

*Primary Examiner* — Thaddeus B Cox
(74) *Attorney, Agent, or Firm* — McGrath North Mullin & Kratz PC LLO; Luke C. Holst

(57) ABSTRACT

The present invention relates in general to the field of hypnotherapy, and more specifically, to a hypnotherapy system for children that utilizes an interactive doll connected to a website and/or downloadable computer software application ("app"), and a method of hypnotherapy for children using the system. One aspect of the present disclosure includes an interactive doll that is configured to play a variety of hypnosis scripts to the child through an audio playback device. The hypnosis scripts may be downloaded to the audio playback device through the connected website/app, wherein the hypnosis scripts are directed to address particular behavioral or emotional issues in the child. The purpose of the invention is to provide a hypnotherapy system and method of hypnotherapy for children that may be conveniently administered to the child in a safe and familiar environment, such as in the child's home or bedroom, without requiring the presence of a hypnotherapist. An additional purpose of the invention is to provide a hypnotherapy system and method of hypnotherapy for children that utilizes an interactive doll that is comforting to the child and that helps retain the attention and focus of the child during a hypnosis session.

19 Claims, 3 Drawing Sheets

(51) Int. Cl.
*G06F 3/16* (2006.01)
*A63H 3/28* (2006.01)
*A63H 3/02* (2006.01)

(52) U.S. Cl.
CPC ..... *G06F 3/165* (2013.01); *A61M 2021/0027* (2013.01); *A61M 2205/3375* (2013.01); *A61M 2205/3584* (2013.01); *A61M 2205/59* (2013.01); *A63H 3/02* (2013.01); *A63H 2200/00* (2013.01)

(56) References Cited

U.S. PATENT DOCUMENTS

| | | |
|---|---|---|
| 5,489,231 A | 2/1996 | Leyser |
| 6,000,987 A | 12/1999 | Belin et al. |
| 6,692,330 B1 | 2/2004 | Kulick |
| 6,940,432 B1 * | 9/2005 | Hall .............. A63H 3/003 341/110 |
| 6,962,517 B2 | 11/2005 | Murray |
| 7,946,901 B2 | 5/2011 | Roberts |
| 8,230,630 B2 | 7/2012 | Storch |
| 8,943,721 B2 | 2/2015 | Storch |
| 9,149,729 B2 | 10/2015 | Storch |
| 2004/0161732 A1 | 8/2004 | Stump et al. |
| 2007/0166678 A1 | 7/2007 | Browning |
| 2008/0287033 A1 | 11/2008 | Steinberg |
| 2008/0305710 A1 | 12/2008 | Roberts |
| 2011/0070805 A1 | 3/2011 | Islava |
| 2012/0252305 A1 | 10/2012 | Sandholt |
| 2013/0344839 A1 * | 12/2013 | Roach .............. H04L 67/02 455/344 |
| 2014/0038489 A1 * | 2/2014 | Sharma .............. A63H 3/28 446/175 |
| 2014/0256214 A1 * | 9/2014 | Ramamoorthy ....... A63H 3/003 446/297 |
| 2015/0118666 A1 | 4/2015 | Rokjer |
| 2015/0248270 A1 * | 9/2015 | Lang .............. G16H 20/70 707/821 |
| 2016/0121229 A1 * | 5/2016 | Guo .............. A63H 3/28 446/175 |
| 2016/0220913 A1 * | 8/2016 | Nanda .............. G05B 15/02 |
| 2017/0039045 A1 * | 2/2017 | Abrahami .............. A61P 3/04 |
| 2018/0117484 A1 * | 5/2018 | McCart-Pollak ...... A63H 30/04 |
| 2019/0015755 A1 * | 1/2019 | Marshall, Jr. .......... A63H 3/02 |

\* cited by examiner

HYPNOTHERAPY SYSTEM UTILIZING AN INTERACTIVE DOLL AND METHOD OF HYPNOTHERAPY FOR CHILDREN

FIELD OF THE INVENTION

The present invention relates in general to the field of hypnotherapy, and more specifically, to a hypnotherapy system for children that utilizes an interactive doll connected to a website and/or downloadable computer software application ("app"), and a method of hypnotherapy for children using the system. The interactive doll of the hypnotherapy system includes an audio playback device having audio input means, audio output means, and memory. Through the website/app, the memory of the audio playback device may be loaded with a plurality of hypnosis scripts that address a variety of child behavioral or emotional issues. The plurality of hypnosis scripts may be played through the audio playback device of the interactive doll to administer hypnotherapy to a child. The purpose of the invention is to provide a system and method that may administer hypnotherapy to the child in a calm and comforting manner by playing hypnosis scripts through the interactive doll. The interactive doll is configured to help retain the attention and focus of the child during hypnotherapy. Hypnotherapy may therefore be administered to the child in a safe and familiar environment, such as in the child's home or bedroom, without requiring the presence of a hypnotherapist. An additional purpose of the invention is to provide a hypnotherapy system and method of hypnotherapy for children that is easy to operate, inexpensive to purchase, and convenient to administer to the child.

BACKGROUND OF THE INVENTION

Hypnosis can play an important role in the advancement of health, the improvement of self-confidence, and the breaking of harmful habits in the human condition. Indeed according to the American Society of Clinical Hypnosis ("ASCH"), the "state of inner absorption, concentration and focused attention" through hypnosis may even help patients use their minds more powerfully. See Sarah Klein, *Science-Backed Health Benefits of Hypnosis*, HUFFINGTON POST, Jul. 2, 2014, available at https://www.huffpost.com/entry/hypnosis-health-benefits_n_5523210. Hypnotherapy, also called medical hypnosis, utilizes a hypnotherapist to facilitate verbal repetition and/or mental imagery to induce a "trance-like state" of increased focus. According to the Mayo Clinic, the process of hypnotherapy is described as calm and relaxing, which opens a patient up to the power of suggestion. Id.

A few of the science-backed benefits of hypnotherapy include the following:
  The improvement of deep sleep and treatment of insomnia without the use of sleep-inducing drugs and adverse side effects;
  The ease of symptoms associated with irritable bowel syndrome;
  The management of pain and stress associated with a number of conditions, such as fibromyalgia, arthritis, cancer, giving birth, headaches, and medical procedures;
  The treatment of anxieties, phobias, disabilities, post-traumatic stress disorder, anger, sexual issues, mourning, and depression;
  Assistance with overcoming harmful habit disorders, such as smoking, over-eating, alcoholism, and drug addiction;
  The treatment of asthma, hypertension, tinnitus, and enuresis; and
  The improvement of self-confidence, self-reliance, and self-control.

The same benefits of hypnotherapy listed above may also be applied to children.

Having vivid imaginations, children are generally more receptive to hypnosis as compared to adults. Hypnotherapy can therefore be an effective treatment for a variety of problems, issues and disorders uniquely associated with children, including the following:
  Learning deficiencies;
  Bed-wetting;
  Poor academic performance;
  Thumb-sucking;
  Fear of the dark;
  Death of a parent or loved one;
  Dealing with parents that are divorcing;
  Separation anxiety;
  Anxiety and stress associated with facing a medical procedure;
  Social problems with peers;
  Attention deficit disorders;
  Hair pulling/nail biting;
  Enhanced creativity;
  Nightmares, night terrors; and
  Sports improvement and/or enhancement;

While the aforementioned benefits of hypnotherapy in children are highly sought-after, unfortunately, the existing methods of administering hypnotherapy to children are quite problematic. For example, hypnotherapy has traditionally been administered in a hypnotherapist's office, wherein successful treatment requires the patient to remain focused and relaxed during a hypnosis session. Such traditional methods of hypnotherapy treatment are therefore in direct conflict with a child's personality, in particular, the fact that children become easily distracted in new environments and are generally anxious around strangers. For this reason, hypnotherapy sessions with children often require extra patience and expense to allow time for the child to become accustomed to his/her environment, comfortable around the hypnotherapist and relaxed during a hypnosis session. Therefore the financial, time and travel expense can be cost prohibitive for treating children with in-person hypnotherapy sessions.

Pre-recorded hypnosis sessions offer two distinct advantages over in-person hypnotherapy sessions: affordability and availability. Self-hypnosis audio recordings, or hypnosis scripts, are significantly less expensive than a visit with a hypnotherapist. Self-hypnosis audio recordings can also be listened to at anytime and anywhere, often in the convenience of one's own home, and are immediately available. Another advantage is that self-hypnosis audio recordings can be listened to several times daily or weekly, depending on the needs of the patient. While the benefits of self-hypnosis audio recordings are notable, however, there are also significant drawbacks to using self-hypnosis audio recordings with children. Indeed, currently-available self-hypnosis audio recordings are "primarily for adults" and "not intended to be used by children." Barrie St. John, "Hypnotherapy for Children—Is Hypnosis Suitable?" (Nov. 2, 2015), available at http://www.selfhypnosis.com/hypnotherapy-for-children/.

There are many reasons why currently-available self-hypnosis audio recordings are not intended for children. For example, children typically do not have the maturity level needed to listen to self-hypnosis audio recordings on simple, non-interactive audio devices (e.g., MP3 and CD players) because of the recording's inherently repetitive nature. Not to be confused with children's audio-books that consist of entertaining stories with exciting sound-effects, self-hypnosis audio recordings require patients to remain relaxed during a session and focused on the repetition of spoken words and suggestions while in a hypnotic state. Thus, without interaction, children often lack the requisite attention skills needed for effective hypnotherapy treatment while listening to self-hypnosis audio recordings. Another reason why currently-available self-hypnosis audio recordings are not intended for children is because such recordings only offer a generalized approach to the most common conditions, without accounting for the listener's age, gender, or details about prevalent issues. An in-person visit with a professional hypnotherapist, by contrast, offers personal interaction with the child. This personal interaction helps retain the attention and focus of the child during hypnotherapy. This personal interaction also provides hypnotherapy treatment that is tailor-made to the child's specific needs, age and gender, which is not achieved by currently available self-hypnosis audio recordings.

Thus, a desire remains to provide a hypnotherapy system and method of hypnotherapy for children that is interactive to help retain the attention and focus of the child. A desire further remains to provide a hypnotherapy system and method of hypnotherapy for children that may be tailor-made to the child's specific needs, age and gender. A desire further remains to provide a hypnotherapy system and method of hypnotherapy for children that may be offered in a familiar environment, such as the child's home or bedroom, to decrease a child's anxiety during a hypnosis session and facilitate relaxation. A desire also remains to provide a hypnotherapy system and method of hypnotherapy for children that is convenient to administer without requiring the presence of a hypnotherapist.

BRIEF SUMMARY OF THE INVENTION

Therefore, it is a principal object, feature, and/or advantage of the present disclosure to overcome the aforementioned deficiencies in the art and provide a hypnotherapy system and method of hypnotherapy for children that utilizes an interactive doll that is configured to retain the attention and focus of the child.

Another object, feature, and/or advantage of the present disclosure is to provide a hypnotherapy system and method of hypnotherapy for children that allows for selection of particular hypnosis scripts that address a child's specific needs, age and gender for a tailor-made approach to hypnotherapy.

Yet another object, feature, and/or advantage of the present disclosure is to provide a hypnotherapy system and method of hypnotherapy for children that is convenient to administer without requiring the presence of a hypnotherapist.

A further object, feature, and/or advantage of the present disclosure is to provide a method of administering hypnotherapy to children that may be offered in a familiar environment such as the child's home or bedroom.

A still further object, feature, and/or advantage of the present disclosure is to provide an interactive doll that is familiar and comforting to the child.

Another object, feature, and/or advantage of the present disclosure is to provide an interactive doll that is easy to operate, clean and maintain.

Yet another object, feature, and/or advantage of the present disclosure is to provide a hypnotherapy system and method of hypnotherapy that may be utilized for children of a wide variety of ages.

A further object, feature, and/or advantage of the present disclosure is to provide an interactive doll that includes an audio playback device with audio input means, audio output means and memory for storing a plurality of hypnosis scripts.

A still further object, feature, and/or advantage of the present disclosure is to provide a hypnotherapy system and method of hypnotherapy for children that is configured to allow a user to easily download new hypnosis scripts into an audio playback device having memory via USB or a wireless connection.

Another object, feature, and/or advantage of the present disclosure is to provide a hypnotherapy system and method of hypnotherapy for children that includes a website/app for desktop computers, mobile devices, portable media players, handheld computers or tablets, the website/app configured to operate with the audio playback device.

Yet another object, feature, and/or advantage of the present disclosure is to provide a hypnotherapy system and method of hypnotherapy for children that includes a website/app configured to allow a user to easily select, download, and/or remove particular hypnosis scripts from the memory of an audio playback device.

A further object, feature, and/or advantage of the present disclosure is to provide a hypnotherapy system and method of hypnotherapy for children that is cost-efficient to manufacture and affordable for the everyday consumer.

These and/or other objects, features, and/or advantages of the present disclosure will be apparent to those skilled in the art. The present disclosure is not to be limited to or by these objects, features, and advantages. No single aspect need provide each and every object, feature, or advantage.

According to one aspect of the present disclosure, a hypnotherapy system is provided. The hypnotherapy system comprises an interactive doll, an audio playback device placed removably inside the interactive doll, and a website/app connected to the audio playback device in either a wired or wireless fashion. The hypnotherapy system is configured to play hypnosis scripts to a child through the audio playback device inside the interactive doll to administer hypnotherapy to a child in a safe and familiar environment, such as the child's bedroom or home, without requiring the presence of a hypnotherapist.

According to another aspect of the present disclosure, a method of hypnotherapy for children using the hypnotherapy system is provided. The method includes providing the hypnotherapy system. The method may next comprise providing a child in need of hypnotherapy. The method may include selecting a particular hypnosis script or a plurality of hypnosis scripts to be played on the audio playback device. The method may next comprise administering hypnotherapy to the child by playing at least one hypnosis script though the audio playback device located inside the interactive doll. Hypnotherapy may thus be administered to the child in a safe and familiar environment, such as in the child's home or bedroom, without requiring the presence of a hypnotherapist to help facilitate successful treatment of hypnotherapy during a hypnosis session.

Different aspects may meet different objects of the disclosure. Other objectives and advantages of this disclosure will be more apparent in the following detailed description taken in conjunction with the figures. The present disclosure is not to be limited by or to these objects or aspects. It is to be understood that both the foregoing general description and the following detailed description are exemplary and explanatory only and are not necessarily restrictive of the present disclosure. The accompanying figures, which are incorporated in and constitute a part of the specification, illustrate subject matter of the disclosure. Together, the descriptions and the figures serve to explain the principles of the disclosure.

DESCRIPTION OF FIGURES

FIG. 1 is a schematic view of the hypnotherapy system of the present disclosure.

FIG. 2 is an isometric front view of an interactive doll of the hypnotherapy system of FIG. 1.

FIG. 3 is an isometric front-side view of an audio playback device removed from the interactive doll of FIG. 2.

DETAILED DESCRIPTION OF THE INVENTION

Figure 1:
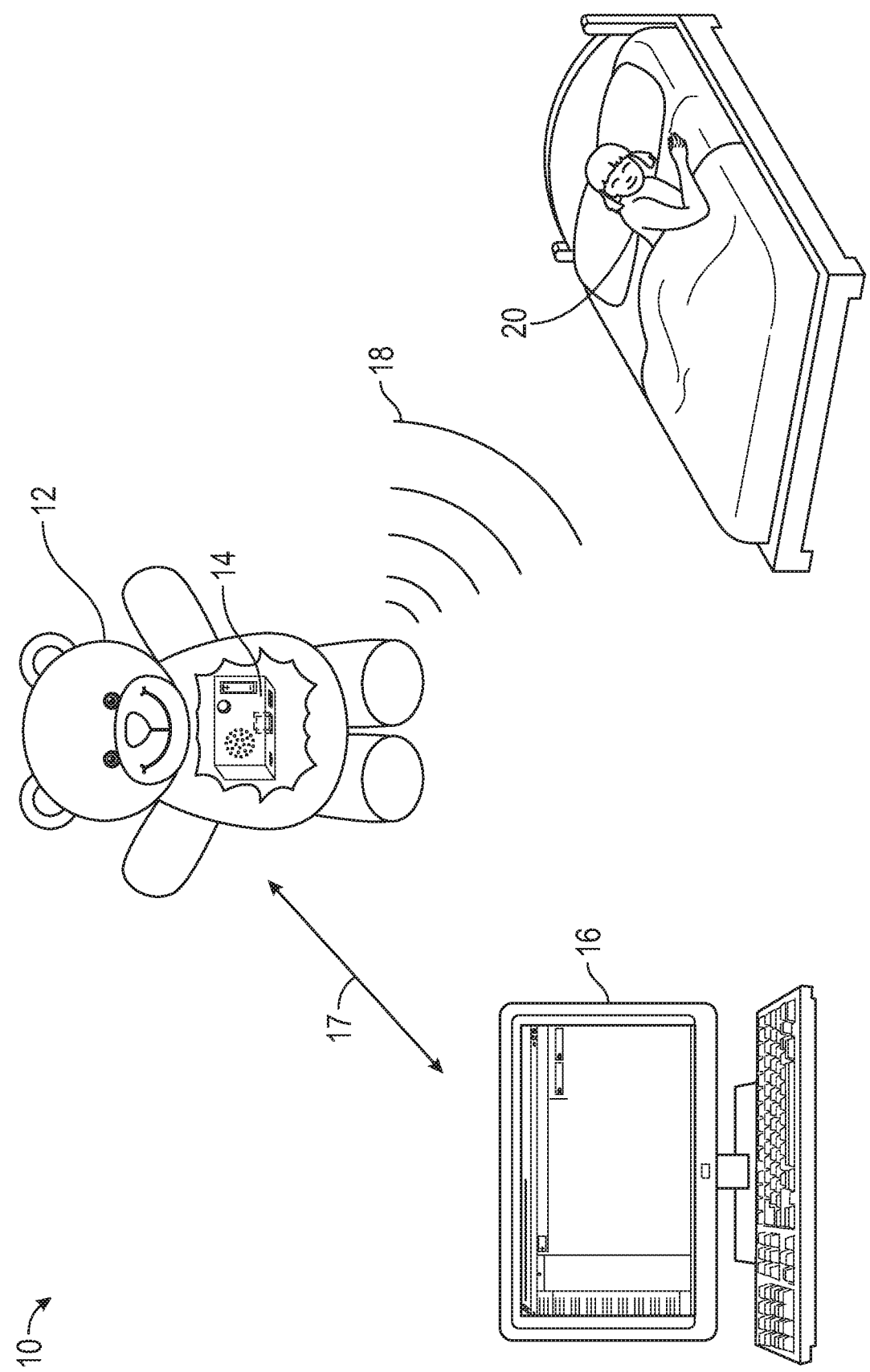
FIGS. 1-3 represent examples of the hypnotherapy system of the present disclosure, and a method of hypnotherapy for children using the system.

FIG. 1 illustrates a schematic view of one aspect of the hypnotherapy system (10) of the present disclosure. In particular, the hypnotherapy system (10) comprises an interactive doll (12), an audio playback device (14) placed removably inside the interactive doll (12), and a website and/or downloadable computer software application ("app") (16) on a desktop computer, mobile device, portable media player, handheld computer or tablet. The website/app (16) may be connected (17) to the audio playback device (14) over a computer network such as the Internet, an intranet, or a local area network in either a wired or wireless fashion (e.g., BLUETOOTH®, Wi-Fi, cellular and/or satellite communication). The hypnotherapy system (10) is configured to play hypnosis scripts (18) to a child (20) in a safe and familiar environment, such as the child's (20) home or bedroom, to administer hypnotherapy to a child. The hypnotherapy system (10) is further configured to allow a user (e.g., parent or caregiver) to administer hypnotherapy to the child (20) through the playing of the hypnosis scripts (18) at a time convenient for the user, without requiring the presence of a hypnotherapist. The hypnotherapy system (10) is still further configured to administer hypnotherapy to the child (20) in a calming and comforting manner by playing the hypnosis scripts (18) through the interactive doll (12). The interactive doll (12) is configured to help retain the attention and focus of the child during hypnotherapy. The hypnotherapy system (10) is configured to only play hypnosis scripts (18) and no other types of sound recordings.

In particular, the hypnosis scripts (18) may incorporate spoken words and narrative, background music, sounds of nature, and other sounds. Each hypnosis script (18) is configured to administer hypnotherapy to a child (20) through the following steps: (a) induction; (b) implementation; (c) suggestability; and (4) positive affirmations. The hypnosis scripts (18) may also address different issues affecting children of a variety of ages. The hypnosis scripts (18) may range in length from ten minutes to one hour, depending on the age of the child (20).

Figure 2:
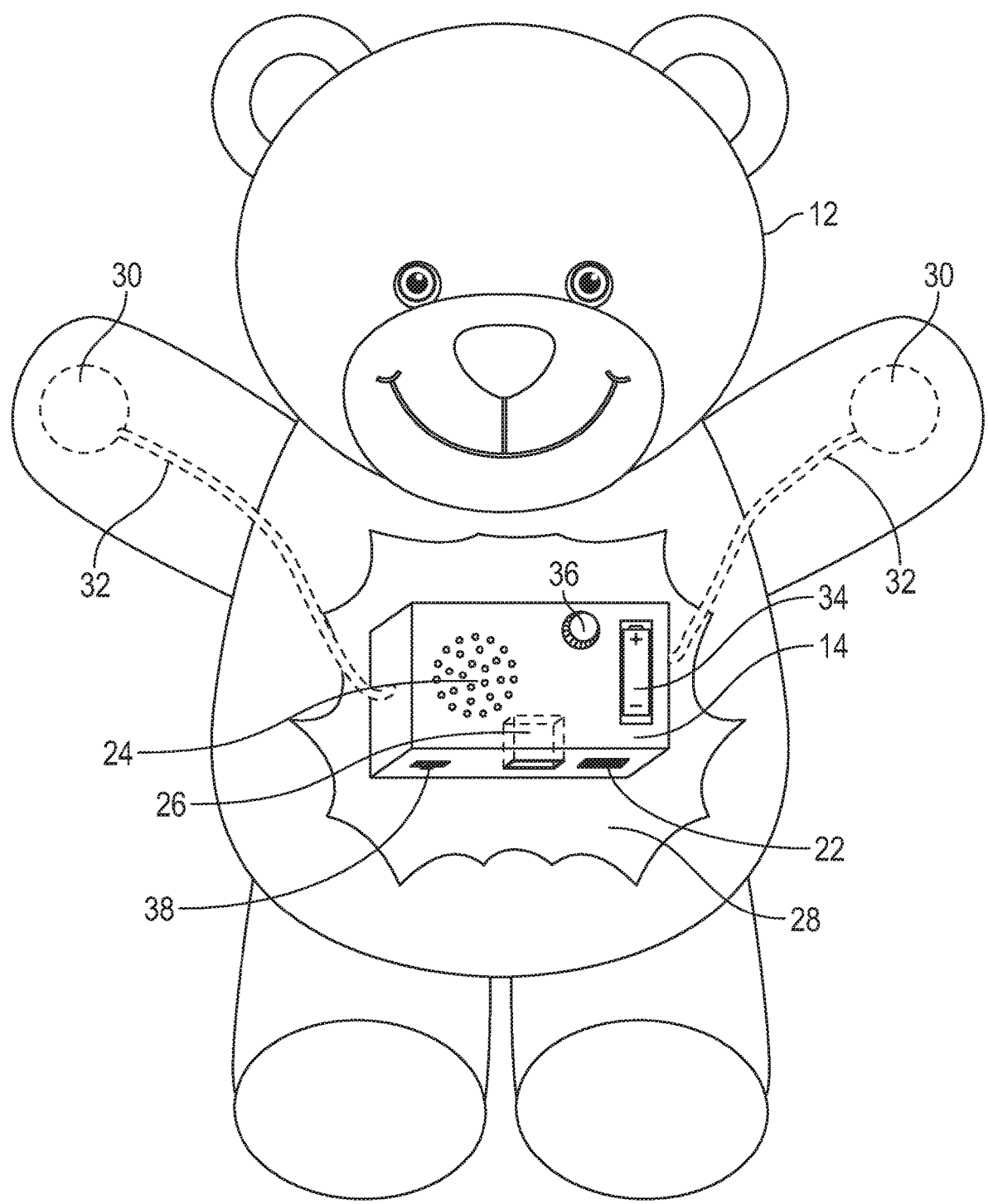

FIG. 2 illustrates an isometric front view of the interactive doll (12) of the hypnotherapy system (10). In particular, the interactive doll (12) is designed to be visually appealing to help retain the attention and focus of the child (20) during hypnotherapy. For example the interactive doll (12) may comprise a soft plush toy or stuffed animal, BARBIE® doll, action figure, or any other type of doll that is capable of being hugged, loved and held by the child (20). The interactive doll (12) may comprise the audio playback device (14). The audio playback device (14) may include an audio input means (22), audio output means (24), and memory (26). The audio playback device (14) may be configured to store and play back hypnosis scripts (18) in an analog or digital recording format. The audio playback device (14) may be removably concealed inside the interactive doll (12), such as in a head or torso portion of the interactive doll (12), to provide a perception that the hypnosis scripts (18) when played are coming from the interactive doll (12). In particular, the audio playback device (14) may be removably concealed inside a pocket (28) of the interactive doll (12), wherein the audio playback device (14) may be secured in position via a VELCRO® strip, buttons, a zipper, or other capable means that provide quick access and retrieval of the audio playback device (14) from the interactive doll (12). Placing the audio playback device (14) inside the pocket (28) of the interactive doll (12) allows for the interactive doll (12) to remain soft and squeezable, wherein the audio playback device (14) is cushioned inside the pocket (28) of the interactive doll (12).

Shown in FIG. 2, the audio playback device (14) may further comprise activation buttons (28) connected to the audio playback device (14) by wiring (30). The remote activation button(s) (28) are configured to start and stop the playing of hypnosis scripts (18) by the audio playback device (14). For example, the remote activation button(s) (28) may be located at an end of the arms, or "hands," of the interactive doll (12). The remote activation button(s) (28) may be configured so that squeezing a first hand of the interactive doll (12) activates the remote activation button (28) to start the playing of a hypnosis script (18). The remote activation button(s) (28) may also be configured so that squeezing a second hand of the interactive doll (12) deactivates the remote activation button (28) to stop the playing of the hypnosis script (18). The wiring (32) electronically connects the remote activation button(s) (30) to the audio playback device (14). Alternatively, the remote activation button(s) (30) may be located on independent devices wirelessly connected to the audio playback device (14) through infrared, radio, BLUETOOTH® or Wi-Fi transmitters. It is contemplated that additional interactive features may also be incorporated into the interactive doll (12), such as automated mechanical movements of the arms, legs, head, mouth and eyes to further help retain the attention and focus of the child (20) during hypnotherapy.

Figure 3:
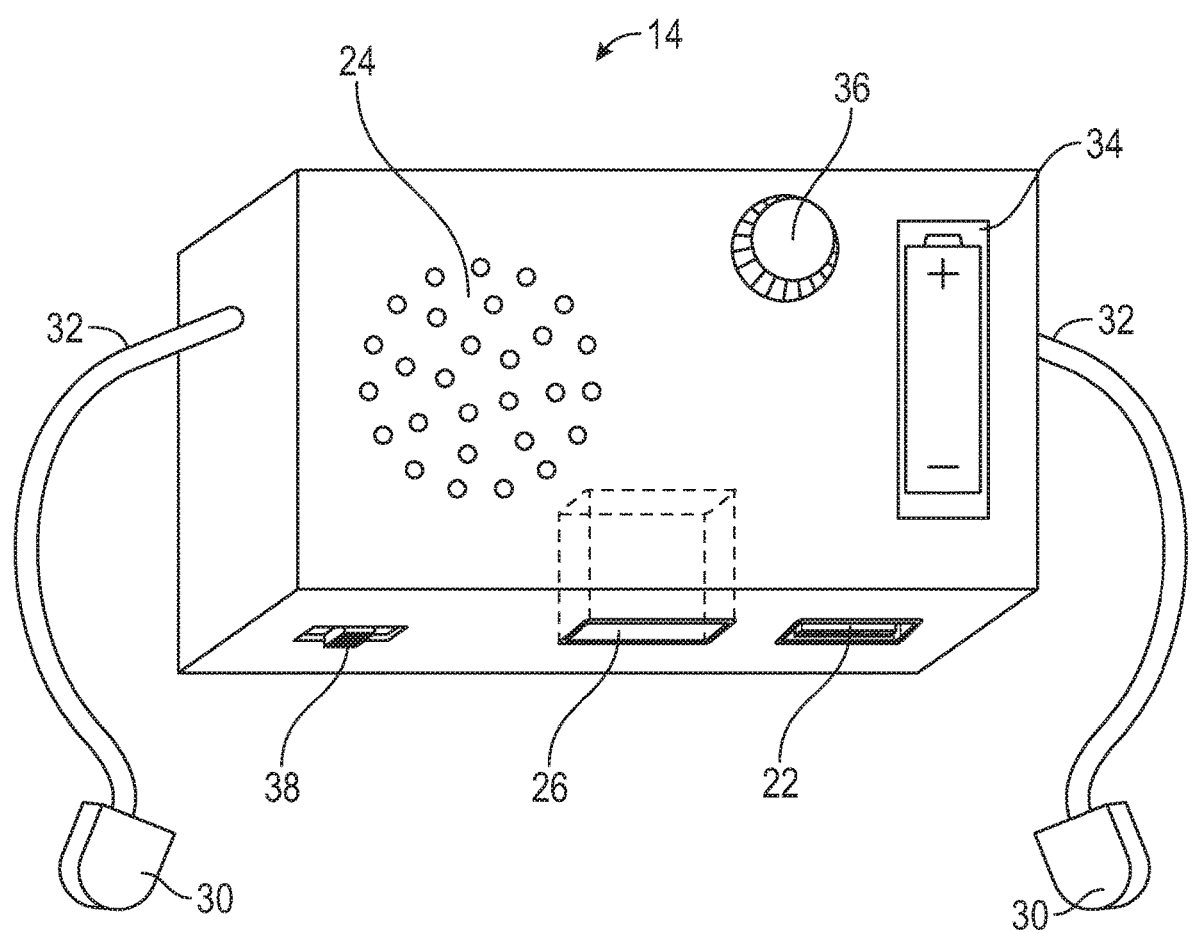

FIG. 3 illustrates a front-side view of the audio playback device (14) removed from the interactive doll (12). In particular, the audio input means (22) of the audio playback device (14) may comprise an auxiliary jack and cable, a USB port and cable, and/or a transceiver configured to connect the audio playback device (14) to a desktop computer, mobile device, portable media player, handheld computer or tablet over a computer network such as the Internet, an intranet, or a local area network in either a wired or wireless fashion (e.g., BLUETOOTH®, Wi-Fi, cellular and/ or satellite communication). The audio input means (22) is configured to allow a plurality of hypnosis scripts (18) to be transferred from the website/app (16) to the memory (26) of the audio playback device (14), or removed from the memory (26) of the audio playback device (14) using the website/app (16).

Shown in FIG. 3, the audio output means (24) of the audio playback device (14) may comprise a single speaker or a plurality of speakers configured to bring high quality sound to a room when the hypnosis scripts (18) are played. The speakers are also configured to be compatible with the English language or any other language that may be utilized in the hypnosis scripts (18).

Further shown in FIG. 3, the memory (26) of the audio playback device (14) may be capable of storing, adding, removing and/or replacing a plurality of hypnosis scripts (18) in a database(s). Such actions may be performed by a local software application, processor and database(s) on the audio playback device (14). The memory (26) may permanently reside inside the audio playback device (14) or the memory (26) may be insertable and removable from the audio playback device (14), such as utilizing a memory stick or memory card. Alternatively or in addition thereto, the plurality of hypnosis scripts (18) may be remotely stored in memory (26) on a cloud database(s) and/or on a hard drive of the desktop computer, mobile device, portable media player, handheld computer or tablet. In such instances the plurality of hypnosis scripts (18) remotely stored may be streamed to the audio playback device (14) over the computer network in a wired or wireless fashion as detailed above for playback through the audio output means (24).

Also shown in FIG. 3, the audio playback device (14) may include a power supply (34), volume control (36), and an on/off switch (38). The power supply (34) is configured to supply electrical power to the audio playback device (14), and may comprise a conventional 1.5 volt battery, an AA or AAA-sized battery, or any other compatible battery that is removable, disposable, and replaceable. Alternatively, the power supply (34) may comprise a battery that is rechargeable. The volume control (36) may comprise a dial that is configured to be gripped and rotated by the user to adjust the overall volume of the hypnosis scripts (18) being played through the audio output means (24) of the audio playback device (14). Alternatively or in addition thereto, the overall volume may be remotely adjusted by the user through the website/app (16). The on/off switch (38) may be configured to allow the user to manually turn the audio playback device (14) on or off to conserve the power supply (34).

The website/app (16) may be configured to allow the user to select a plurality of hypnosis scripts (18) for download and storage in the memory (26) of the audio playback device (14). Alternatively or in addition thereto, the website/app (16) may be configured to allow the user to select a plurality of hypnosis scripts (18) for download and storage in the cloud database and/or on the hard drive of the desktop computer, mobile device, portable media player, handheld computer or tablet.

The website/app (16) of the hypnotherapy system (10) may be configured to divide the plurality of hypnosis scripts (18) into various categories and subcategories for ease of selection by the user. For exemplary purposes only, and not to limit the present disclosure, the plurality of hypnosis scripts (18) may be divided into different categories for boys and girls, into different subcategories depending on the age of the child, and into different subcategories addressing child behavioral or emotional issues.

In particular, the web site/app (16) may be configured to allow the user to make a first selection for hypnosis scripts (18) that are gender specific, such as selecting between the following categories: (a) girls; and (b) boys. The website/app (16) may be configured to allow the user to make a second selection for hypnosis scripts (18) that address children in certain age groups, such as selecting among the following subcategories: (a) preschool, ages 3-5; (b) early elementary, ages 6-8; (c) elementary, ages 9-12; and (d) adolescents, ages 13-18. The website/app (16) may further be configured to allow the user to make a third selection for hypnosis scripts (18) that address different issues affecting children, such as selecting between the following subcategories: (a) child behavioral issues; and (b) child emotional issues.

If the user selects the subcategory for hypnosis scripts (18) that address child behavioral issues, additional selection options may be provided to allow the user to select particular hypnosis script(s) (18) that address one or more of the following child behavioral issues: fingernail biting; thumb-sucking; tantrums; sleep disturbances; sibling rivalry; toilet training; toy sharing; bed-wetting; nose picking; poor grades; school attendance; lying; and sports improvement/enhancement; academic difficulties in productivity or skills; accepting others; asking for help; trusting; assertiveness/appropriate expression of emotion; performing tasks/chores that the child does not feel like performing; setting boundaries; blaming others; controlling relationships; problems making friends; fusion between siblings; holding onto feces; oppositional/rebellious attitudes; over reactive; peer pressure; prejudice; problems solving ability/resources; problems with school (e.g., daydreamer, problems focusing, fear of making mistakes, inability to access information, making friends, problems with learning, school refusal, refusal to accept help); social skills; speaking/focus problems; stealing; trying new things; withdrawn; shyness; and self-protective.

On the other hand, if the user selects the subcategory for hypnosis scripts (18) that address child emotional issues, additional selection options may be provided to allow the user to select particular hypnosis script(s) (18) that address one or more of the following child emotional issues: separation anxiety; social anxiety; school phobias; death/loss; depression; divorce of parents; trauma; anxiety with medical procedures; coping with physical pain; emotional coping; nightmares/terrors; self-esteem; self-confidence; attention deficit disorders; defying authority; phobias; obsessions/compulsions; worry; school violence; fear of animals; promiscuity; spectrum disorders (i.e., autism); self-worth; abusive relationships; adoption; anger; child abuse/disclosure; child abuse/healing symptoms; child abuse/seeing abuser clearly; child abuse/suspected; child abuse/taking on characteristics of the abuser; cognitive restructuring of attitudes and beliefs; court issues (e.g., putting experiences into words, understanding the difference between a truth and a lie); disorganization; distorted perception of reality; dysfunctional family; eating disorders; emotionally younger/stuck; external focus/self-value; fear of authority; foster care/foster children; fragmental thought process; letting go of past problems; illness/terminal; impulsive; joy/happiness; lack of being loved; marital issues; domestic violence; misinterpreting actions of others; disassociation; never satisfied; optimistic and pessimistic; obsessive thoughts; attachment disorder; parents (e.g., constant conflict between, controlling, inappropriate coping, chronic or terminal illness, raging); perceptions/distorted; perfectionism/fear of making mistakes; PTSD (e.g., absence of fantasy, no sense of future, lack of goals, amnesia of all or part of trauma, concentration, reading, math and speech, making decisions, distorted perception, excessive anger, anxiety, fear, flashbacks, flat affect, stuttering, shutting down of emotions, problems sleeping, isolation); removing destructive anchors and triggers; self-understanding; self-abuse; self-blame; self-hate; sense of self or lack of; destructive relationships; shame; strengths/understanding one's own strength; taking on others problems; problem thinking (e.g., fragmented, dissociation, amnesia, rigid, thought disturbances); and depression.

The examples of hypnosis scripts (18) listed above are for exemplary purposes only, as it is contemplated that hypnosis scripts (18) addressing other issues in children for other categories and subcategories may also be utilized in the present disclosure.

The website/app (16) may be further configured to allow the user to select a particular hypnosis script (18) or a plurality of hypnosis scripts (18) to be played on the audio playback device (14) to provide hypnotherapy to the child (20). Additionally, the website/app (16) may be configured to allow the user to create a playlist of a plurality of hypnosis scripts (18) for playback on the audio playback device (14), to select a particular hypnosis script (18) to be repeated a set number of times on the audio playback device (14), to start/stop playback of a hypnosis script (18) on the audio playback device (14), and to add/delete hypnosis scripts (18) from the memory (26). Alternatively or in addition thereto, the audio playback device (14) may be configured to allow the user to perform the same actions listed above via an interactive touch screen, display, or buttons on the audio playback device (14).

In this manner, the hypnotherapy system (10) of the present disclosure may administer hypnotherapy to the child (20) in a calming and comforting manner by playing hypnosis scripts (18) through the interactive doll (12), which may become the child's beloved toy. The interactive doll (12) is further configured to help retain the attention and focus of the child (20) during hypnotherapy. Hypnotherapy may therefore be administered to the child (20) in a safe and familiar environment, such as in the child's home or bedroom, without requiring the presence of a hypnotherapist to help facilitate successful treatment of hypnotherapy during a hypnosis session.

Another aspect of the present disclosure is a method of hypnotherapy for children using the hypnotherapy system (10) of FIGS. 1-3. In particular, the method may comprise providing the hypnotherapy system (10) of FIGS. 1-3. The method may next comprise providing a child (20) in need of hypnotherapy. Notably, the child (20) may have previously had problems during traditional hypnosis sessions offered in an unfamiliar environment such as a hypnotherapist's office. The method may also comprise selecting on the website/app a plurality of hypnosis scripts (18) for download and storage in the memory (26) of the audio playback device (14). Alternatively or in addition thereto, the method may comprise selecting a plurality of hypnosis scripts (18) for download and storage in the cloud database and/or on the hard drive of the desktop computer, mobile device, portable media player, handheld computer or tablet.

The method may next include making a first selection on the website/app (16) for hypnosis scripts (18) that are gender specific, in particular, making a first selection between the following categories: (a) girls; and (b) boys. The method also comprises making a second selection on the website/app (16) for hypnosis scripts (18) that address children in certain age groups, such as selecting among the following categories depending on the age of the child: (a) preschool, ages 3-5; (b) early elementary, ages 6-8; (c) elementary, ages 9-12; and (d) adolescents, ages 13-18. The method further comprises making a third selection on the website/app (16) for hypnosis scripts (18) that address different issues affecting children, such as selecting between the following categories: (a) child behavioral issues; and (b) child emotional issues.

Depending on the choice of the third selection, additional selections may be made for selecting particular hypnosis scripts (18) that address at least one of the following child behavioral issues: fingernail biting; thumb-sucking; tantrums; sleep disturbances; sibling rivalry; toilet training; toy sharing; bed-wetting; nose picking; poor grades; school attendance; lying; and sports improvement/enhancement; academic difficulties in productivity or skills; accepting others; asking for help; trusting; assertiveness/appropriate expression of emotion; performing tasks/chores that the child does not feel like performing; setting boundaries; blaming others; controlling relationships; problems making friends; fusion between siblings; holding onto feces; oppositional/rebellious attitudes; over reactive; peer pressure; prejudice; problems solving ability/resources; problems with school (e.g., daydreamer, problems focusing, fear of making mistakes, inability to access information, making friends, problems with learning, school refusal, refusal to accept help); social skills; speaking/focus problems; stealing; trying new things; withdrawn; shyness; and self-protective.

On the other hand, if the third selection is made for hypnosis scripts (18) that address child emotional issues, additional selections may be made for selecting particular hypnosis scripts (18) that address at least one of the following child emotional issues: separation anxiety; social anxiety; school phobias; death/loss; depression; divorce of parents; trauma; anxiety with medical procedures; coping with physical pain; emotional coping; nightmares/terrors; self-esteem; self-confidence; attention deficit disorders; defying authority; phobias; obsessions/compulsions; worry; school violence; fear of animals; promiscuity; spectrum disorders (i.e., autism); self-worth; abusive relationships; adoption; anger; child abuse/disclosure; child abuse/healing symptoms; child abuse/seeing abuser clearly; child abuse/suspected; child abuse/taking on characteristics of the abuser; cognitive restructuring of attitudes and beliefs; court issues (e.g., putting experiences into words, understanding the difference between a truth and a lie); disorganization; distorted perception of reality; dysfunctional family; eating disorders; emotionally younger/stuck; external focus/self-value; fear of authority; foster care/foster children; fragmental thought process; letting go of past problems; illness/terminal; impulsive; joy/happiness; lack of being loved; marital issues; domestic violence; misinterpreting actions of others; disassociation; never satisfied; optimistic and pessimistic; obsessive thoughts; attachment disorder; parents (e.g., constant conflict between, controlling, inappropriate coping, chronic or terminal illness, raging); perceptions/distorted; perfectionism/fear of making mistakes; PTSD (e.g., absence of fantasy, no sense of future, lack of goals, amnesia of all or part of trauma, concentration, reading, math and speech, making decisions, distorted perception, excessive anger, anxiety, fear, flashbacks, flat affect, stuttering, shutting down of emotions, problems sleeping, isolation); removing destructive anchors and triggers; self-understanding; self-abuse; self-blame; self-hate; sense of self or lack of; destructive relationships; shame; strengths/understanding one's own strength; taking on others problems; problem thinking (e.g., fragmented, dissociation, amnesia, rigid, thought disturbances); and depression.

The examples of hypnosis scripts (18) listed above are for exemplary purposes only, as it is contemplated that hypnosis scripts (18) addressing other issues in children for other categories and subcategories may also be utilized in the present disclosure.

The method may also include selecting a particular hypnosis script (18) or a plurality of hypnosis scripts (18) from the categories and subcategories listed above to be played on the audio playback device (14). Additionally, the method may comprise creating a playlist of a plurality of hypnosis scripts (18) for playback on the audio playback device (14), selecting a particular hypnosis script (18) to be repeated a set number of times on the audio playback device (14), starting/stopping playback of a hypnosis script (18) on the audio playback device (14), and adding/deleting hypnosis scripts (18) from the memory (26).

The method may next comprise administering hypnotherapy to the child (20) by playing at least one hypnosis script (18) though the audio playback device (14) located inside the interactive doll (12). The interactive doll (12) is configured to help retain the attention and focus of the child (20) during hypnotherapy. Hypnotherapy may thus be administered to the child (20) in a safe and familiar environment, such as in the child's home or bedroom, without requiring the presence of a hypnotherapist to help facilitate successful treatment of hypnotherapy during a hypnosis session.

The hypnotherapy system (10) and method of hypnotherapy for children using the hypnotherapy system (10) is universally applicable to children of all ages, genders, sexual orientations, ethnicities, social-economic backgrounds, and religious beliefs. Furthermore, while intended for children, the hypnotherapy system (10) and method of hypnotherapy may also be used for adults and the elderly. Although the disclosure has been described and illustrated with respect to preferred aspects thereof, it is not to be so limited since changes and modifications may be made therein which are within the full intended scope of the disclosure.

What is claimed is:

1. A hypnotherapy system, comprising:
   an interactive doll;
   a website and/or downloadable computer software application ("website/app") on a desktop computer, mobile device, portable media player, handheld computer, or tablet;
   a plurality of hypnosis scripts on the website/app;
   wherein each hypnosis script of the plurality of hypnosis scripts is configured to administer hypnotherapy through steps comprising:
   a) induction;
   b) implementation;
   c) suggestibility; and
   d) positive affirmations;
   the website/app connected to an audio playback device via wires or wirelessly;
   the audio playback device removably concealed inside the interactive doll;
   the audio playback device comprising:
   a) memory;
   b) an audio input means configured to connect the website/app to the audio playback device for transferring the plurality of hypnosis scripts from the website/app and storing the plurality of hypnosis scripts in the memory;
   c) an audio output means configured to play the plurality of hypnosis scripts;
   d) a power supply configured to supply power to the audio playback device;
   e) a volume control configured to adjust volume of the audio output means;
   f) an on/off switch configured to conserve power to the audio playback device; and
   the audio playback device configured to play at least one hypnosis script selected from the plurality of hypnosis scripts to administer hypnotherapy.

2. The hypnotherapy system of claim 1, wherein the website/app comprises:
   a) a category of the plurality of hypnosis scripts addressed to boys; and
   b) a category of the plurality of hypnosis scripts addressed for girls;
   wherein the website/app is configured to allow a user to select between each of these categories.

3. The hypnotherapy system of claim 2, wherein the website/app comprises:
   a) a subcategory of the plurality of hypnosis scripts addressed to children of ages 3-5;
   b) a subcategory of the plurality of hypnosis scripts addressed to children of ages 6-8;
   c) a subcategory of the plurality of hypnosis scripts addressed to children of ages 9-12; and
   d) a subcategory of the plurality of hypnosis scripts addressed to children of ages 13-18;
   wherein the website/app is configured to allow the user to select between each of these subcategories.

4. The hypnotherapy system of claim 2, wherein the website/app comprises:
   a) a subcategory of the plurality of hypnosis scripts addressed to child behavioral issues; and
   b) a subcategory of the plurality of hypnosis scripts addressed to child emotional issues;
   wherein the subcategory of the plurality of hypnosis scripts addressed to child behavioral issues includes at least one of the following: fingernail biting; thumb-sucking; tantrums; sleep disturbances; sibling rivalry; toilet training; toy sharing; bed-wetting; nose picking; poor grades; school attendance; lying; or sports improvement/enhancement;
   wherein the subcategory of the plurality of hypnosis scripts addressed to child emotional issues includes at least one of the following: separation anxiety; social anxiety; school fear; death/loss; depression; divorce of parents; trauma; anxiety with medical procedures; coping with physical pain; emotional coping; nightmares/terrors; self-esteem; self-confidence; attention deficit disorders; defying authority; phobias; obsessions/compulsions; worry; school violence; fear of animals; or promiscuity;
   wherein the website/app is configured to allow the user to select between each of these subcategories.

5. A hypnotherapy system, comprising:
   an interactive doll;
   an audio playback device removably concealed inside the interactive doll;
   a website and/or downloadable computer software application ("website/app");
   the website/app connected to the audio playback device;
   a plurality of hypnosis scripts on the website/app;
   wherein each hypnosis script of the plurality of hypnosis scripts is configured to administer hypnotherapy through steps comprising:
   a) induction;
   b) implementation;
   c) suggestibility; and
   d) positive affirmations; and the audio playback device configured to play at least one hypnosis script selected from the plurality of hypnosis scripts to administer hypnotherapy.

6. The hypnotherapy system of claim 5, wherein the audio playback device comprises:
   a) memory;
   b) an audio input means configured to connect the website/app to the audio playback device for transferring and storing the plurality of hypnosis scripts in the memory; and
   c) an audio output means configured to play the plurality of hypnosis scripts.

7. The hypnotherapy system of claim 6, wherein the audio input means comprises an auxiliary jack and cable, a USB port and cable, or a transceiver.

8. The hypnotherapy system of claim 6, wherein the audio output means comprises at least one speaker.

9. The hypnotherapy system of claim 6, wherein the website/app is configured to allow a user to select at least one hypnosis script from the plurality of hypnosis scripts to be played on the audio playback device to provide hypnotherapy.

10. The hypnotherapy system of claim 5, wherein the website/app comprises:
    a) a category of the plurality of hypnosis scripts addressed to boys; and
    b) a category of the plurality of hypnosis scripts addressed for girls;
    wherein the website/app is configured to allow a user to select between each of these categories.

11. The hypnotherapy system of claim 10, wherein the website/app comprises:
    a) a subcategory of the plurality of hypnosis scripts addressed to children of ages 3-5;
    b) a subcategory of the plurality of hypnosis scripts addressed to children of ages 6-8;
    c) a subcategory of the plurality of hypnosis scripts addressed to children of ages 9-12; and
    d) a subcategory of the plurality of hypnosis scripts addressed to children of ages 13-18;
    wherein the website/app is configured to allow the user to select between each of these subcategories.

12. The hypnotherapy system of claim 10, wherein the website/app comprises:
    a) a subcategory of the plurality of hypnosis scripts addressed to child behavioral issues; and
    b) a subcategory of the plurality of hypnosis scripts addressed to child emotional issues;
    wherein the website/app is configured to allow the user to select between each of these subcategories.

13. The hypnotherapy system of claim 12, wherein the subcategory of the plurality of hypnosis scripts addressed to child behavioral issues includes at least one of the following: fingernail biting; thumb-sucking; tantrums; sleep disturbances; sibling rivalry; toilet training; toy sharing; bedwetting; nose picking; poor grades; school attendance; lying; or sports improvement/enhancement.

14. The hypnotherapy system of claim 12, wherein the subcategory of the plurality of hypnosis scripts addressed to child emotional issues includes at least one of the following: separation anxiety; social anxiety; school fear; death/loss; depression; divorce of parents; trauma; anxiety with medical procedures; coping with physical pain; emotional coping; nightmares/terrors; self-esteem; self-confidence; attention deficit disorders; defying authority; phobias; obsessions/compulsions; worry; school violence; fear of animals; or promiscuity.

15. A method of administering hypnotherapy, the method comprising:
    providing a hypnotherapy system, comprising:
        a) an interactive doll;
        b) an audio playback device removably concealed inside the interactive doll;
        c) a website and/or downloadable computer software application ("website/app");
        d) the website/app connected to the audio playback device;
        e) a plurality of hypnosis scripts on the website/app;
        f) wherein each hypnosis script of the plurality of hypnosis scripts is configured to administer hypnotherapy through steps comprising: (i) induction; (ii) implementation; (iii) suggestibility; and (iv) positive affirmations; and
        g) the audio playback device configured to play at least one hypnosis script selected from the plurality of hypnosis scripts to administer hypnotherapy;
    providing an individual in need of hypnotherapy;
    selecting on the website/app at least one hypnosis script from the plurality of hypnosis scripts for download and storage in the memory of the audio playback device; and
    administering hypnotherapy by playing at least one hypnosis script though the audio playback device located inside the interactive doll.

16. The method of claim 15, further comprising making a first selection of the plurality of hypnosis scripts on the website/app from the following categories:
    a) a category of the plurality of hypnosis scripts addressed to boys; and
    b) a category of the plurality of hypnosis scripts addressed for girls.

17. The method of claim 16, further comprising making a second selection of the plurality of hypnosis scripts on the website/app from the following subcategories:
    a) a subcategory of the plurality of hypnosis scripts addressed to children of ages 3-5;
    b) a subcategory of the plurality of hypnosis scripts addressed to children of ages 6-8;
    c) a subcategory of the plurality of hypnosis scripts addressed to children of ages 9-12; and
    d) a subcategory of the plurality of hypnosis scripts addressed to children of ages 13-18.

18. The method of claim 17, further comprising making a third selection of the plurality of hypnosis scripts on the website/app from the following subcategories:
    a) a subcategory of the plurality of hypnosis scripts addressed to child behavioral issues; and
    b) a subcategory of the plurality of hypnosis scripts addressed to child emotional issues.

19. The method of claim 18, further comprising:
    selecting a particular hypnosis script or a plurality of hypnosis scripts from the subcategories to be played on the audio playback device; and
    administering hypnotherapy to the child by playing at least one hypnosis script though the audio playback device located inside the interactive doll.

* * * * *